United States Patent
Carlini

(10) Patent No.: US 12,115,265 B1
(45) Date of Patent: Oct. 15, 2024

(54) DEVICE AND METHOD FOR STERILIZING OBJECTS SUCH AS MASKS

(71) Applicant: Oven Industries, Inc., Camp Hill, PA (US)

(72) Inventor: Michael D. Carlini, Mohnton, PA (US)

(73) Assignee: Oven Industries, Inc., Camp Hill, PA (US)

( * ) Notice: Subject to any disclaimer, the term of this patent is extended or adjusted under 35 U.S.C. 154(b) by 795 days.

(21) Appl. No.: 17/241,256

(22) Filed: Apr. 27, 2021

Related U.S. Application Data

(60) Provisional application No. 63/016,146, filed on Apr. 27, 2020.

(51) Int. Cl.
*A61L 2/04* (2006.01)
*A61L 2/24* (2006.01)

(52) U.S. Cl.
CPC .................. *A61L 2/04* (2013.01); *A61L 2/24* (2013.01); *A61L 2202/122* (2013.01); *A61L 2202/14* (2013.01)

(58) Field of Classification Search
CPC ..... A61L 2/00; A61L 2/02; A61L 2/04; A61L 2/24; A61L 2202/00; A61L 2202/10; A61L 2202/12; A61L 2202/122; A61L 2202/14
See application file for complete search history.

(56) References Cited

U.S. PATENT DOCUMENTS

| | | | |
|---|---|---|---|
| 8,327,606 B2* | 12/2012 | Kemp | B65B 31/024 422/26 |
| 2009/0107988 A1* | 4/2009 | Kaastra | C03C 8/20 374/185 |
| 2018/0289846 A1* | 10/2018 | Cookson | A61L 2/18 |

\* cited by examiner

*Primary Examiner* — Natasha E Young
(74) *Attorney, Agent, or Firm* — Hooker & Habib, P.C.

(57) ABSTRACT

A sterilizing device includes a heater plate connected to a controller separately spaceable away from the heater plate. The controller regulates heating of the heater plate to a desired operating temperature. The heater plate is placed in a separate container and objects to be sterilized are placed in the container proximate to the heater plate. The heater plate is heated to a sufficient temperature for a sufficient length of time to sterilize the objects in the container.

13 Claims, 3 Drawing Sheets

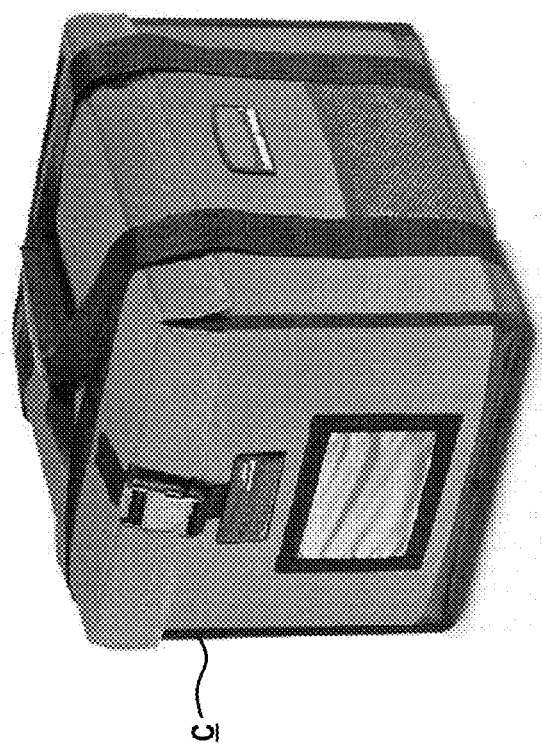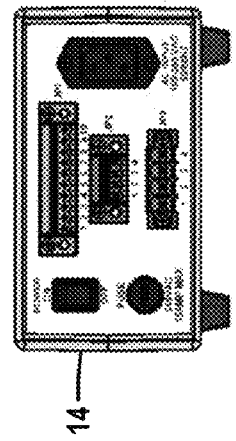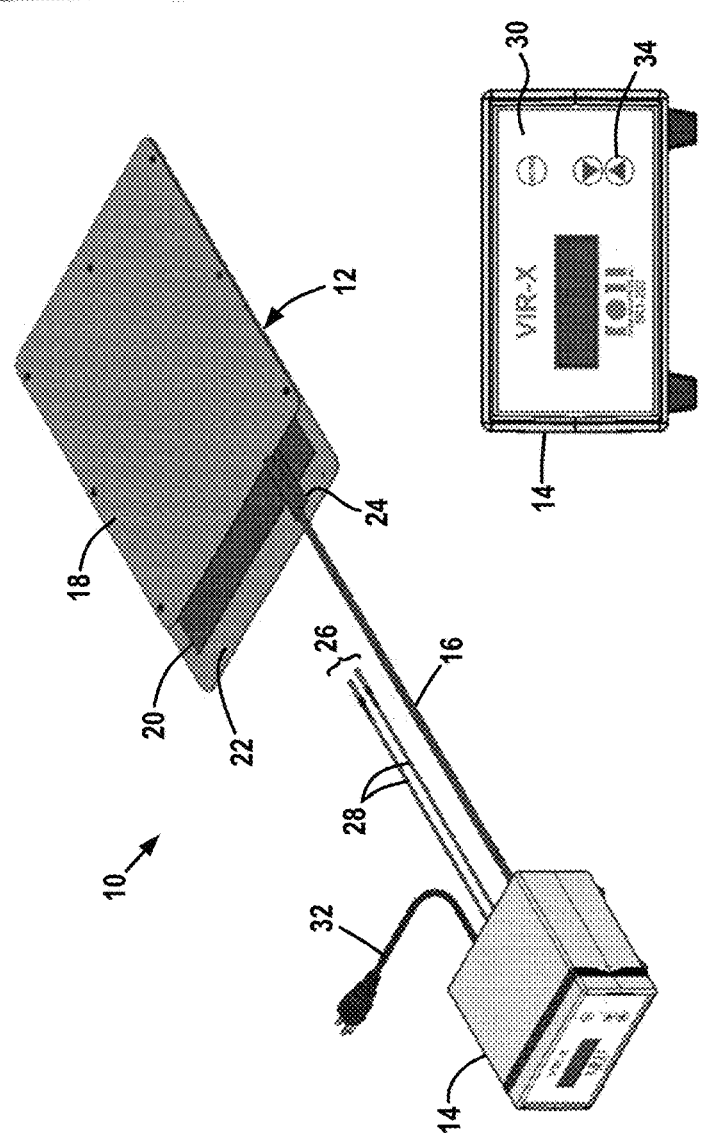

DEVICE AND METHOD FOR STERILIZING OBJECTS SUCH AS MASKS

RELATED APPLICATION

This application claims priority to and the benefit of the filing date of U.S. provisional patent application 63/016,146 filed Apr. 27, 2020 entitled "Device and Method for Sterilizing Objects Such As Masks", which provisional application was on the filing date of this application and is incorporated by reference as if fully set forth herein.

FIELD OF THE DISCLOSURE

The disclosure relates to sterilizing objects, and in particular, to a device and related method useful for sterilizing objects such as face masks.

BACKGROUND OF THE DISCLOSURE

The Covid-19 pandemic has caused a surge in the use of face masks that cover the mouth and nose to reduce the risk of transmittal of the SARS-COV-2 coronavirus. Thus there is a need for a device that can quickly and inexpensively sterilize masks to kill the coronavirus and enable mask reuse.

The device should be easy to use, and should enable the masks to be sterilized in make-shift containers that are that are generally not intended for use with sterilization. In an emergency situation where it is desired to sterilize a large number of masks for days or weeks of an emergency, inexpensive and easily obtainable containers can be kept on hand and used in such emergency situations.

SUMMARY OF THE DISCLOSURE

Disclosed is a sterilizing device and related method for sterilizing objects such as masks. The device is easy to use, and enables objects to be sterilized in make-shift containers that are generally not intended for use with sterilization but are inexpensive and usually readily available for purchase.

The device in accordance with this disclosure includes a heater plate assembly operatively connected to a controller. The heater plate assembly includes a heater plate that generates heat. The heater plate is electrically heated and connected to the controller by a length of flexible electrical conductor. The heater plate can be moved relative to controller to enable the heater plate to be placed within different-sized containers that may be used to hold the objects to be sterilized.

The controller regulates the heat generated by the heater plate. The controller enables s a user to set the desired operating temperature of the heater plate and, in possible embodiments, the time period the heater plate will be energized. For example, the controller may allow the user to set a desired temperature of the heater plate to be maintained at 200 degrees Fahrenheit for a one-half hour period.

The heater plate is placed within a container that will hold the objects to be sterilized. Preferably the container is insulated to resist heat transfer from inside the container to the ambient environment such as an insulated food carrier. Other containers that have been found satisfactory for use with the disclosed sterilization device include pizza boxes and the like.

By providing a heater plate intended to be separate from and not attached to the container itself, many different types of containers can be used to sterilize objects. The containers at manufacture do not have to be intended for use in sterilizing objects as would an oven of a conventional sterilizing oven. The controller can limit the maximum temperature of the heater plate and can energize the heater plate for different lengths of time as required by the different materials forming the containers.

Other objects and features of the disclosure will become apparent as the description proceeds, especially when taken in conjunction with the accompanying drawing sheets illustrating one or more illustrative embodiments.

BRIEF DESCRIPTION OF THE DRAWINGS

FIG. 1 illustrates a sterilizing device in accordance with this disclosure.

FIGS. 2 and 3 are front and rear views of the controller of the sterilizing device shown in FIG. 1.

FIG. 4 illustrates an insulated food container that can be used to hold objects sterilized by the sterilizing device shown in FIG. 1.

DETAILED DESCRIPTION

Figure 5:
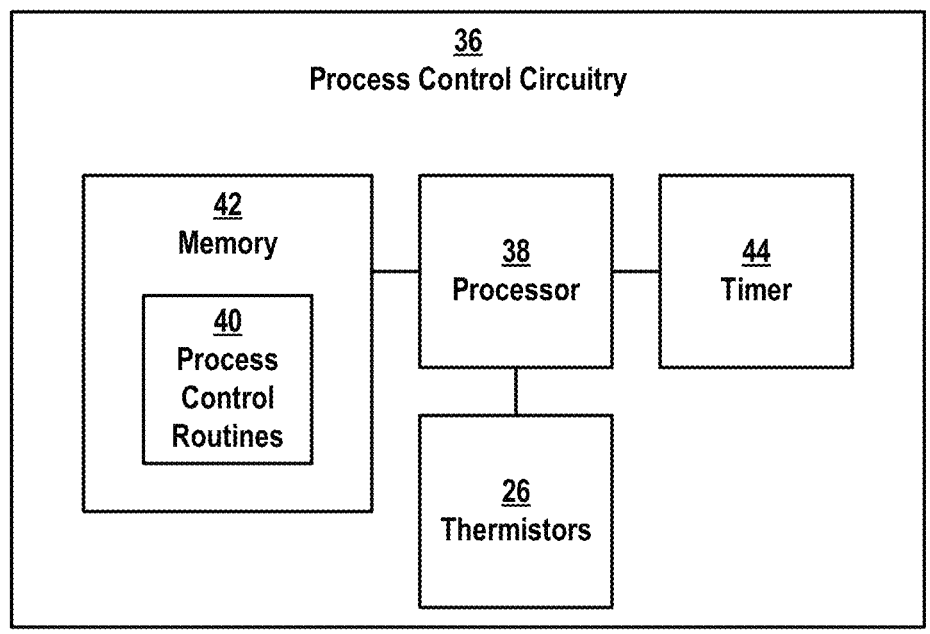
FIG. 5 schematically illustrates the process control circuitry of the controller shown in FIGS. 2 and 3.

FIG. 1 illustrates a sterilizing device 10 in accordance with this disclosure. The sterilizing device 10 includes a heater plate assembly 12 operatively connected to a controller 14 (shown separately in FIGS. 2 and 3) by a length of flexible electrical conductor 16.

The heater plate assembly 12 includes an electrically heated heater plate 18 that overlays a generally flat, planar heating element 20. The heating element 20 is an electric resistance heater disposed on a support plate 22 that supports both the heater plate 18 and the heating element 20.

The electrical conductor 16 extends from the controller 14 and is attached to and is electrically connected to the electrical heater 20 through an electrical connector 24. The controller 14 regulates the current flowing to the heater plate 18 to control and regulate the air temperature in the vicinity of the heater plate 18.

In operation a pair of thermistors 26 are placed proximate to the heater plate 18 in the container to sense the temperature in the container in the vicinity of the heater plate 18. The thermistors 26 form part of the process control circuitry of the controller 14 described in more detail below.

The thermistors 26 may be configured for permanent attachment to the heater plate 18 or the support plate 22. The thermistors 26 are connected to the controller 14 by respective field wires 28 that communicate signals representative of thermistor temperature back to the controller for automatic regulation of the heater plate temperature by the controller 14.

The controller 14 has a front panel 30 for turning on or off the sterilizing device 10. The illustrated device is supplied with AC current using an electrical power cord 32, although other embodiments may use DC current (for example, supplied by a battery) or other type of power supply.

The front panel 30 also displays user controls 34 connected to process control circuitry (described below) of the controller 14 that enables a user to set the desired temperature for to achieve sterilization. For example, a user may set the temperature to 200 degrees Fahrenheit. Higher or lower temperatures may be used depending on the item (s) being sterilized, the operating environment of the heater plate, the types of organisms or contagions being killed by the sterilization, the desired sterilization time, and the like. The illustrated controls 34 also enables a user to set the time period the heater plate 18 is energized.

The controller 14 includes process control circuitry 36 shown in FIG. 4 that include a processor 38 that executes one or more process control routines 40 stored in a memory 42. The control routines 40 may be implemented in any desired software format, such as using object oriented programming, ladder logic, sequential function charts, function block diagrams, or using any other software programming language or design paradigm. The control routines 40 may be stored in any desired type of memory 42, such as random access memory (RAM), or read only memory (ROM). Likewise, the control routines 40 may be hard-coded into, for example, one or more EPROMS, EEPROMs, application specific integrated circuits (ASICs), or any other hardware or firmware elements. Thus, the controller 14 may be configured to implement a control strategy or control routine in any desired manner.

The process control routines 40 use the temperature represented by the signals from the thermistors 26 to automatically control the operating temperature of the heating plate 18. The process control circuitry 36 also includes a timer 44 that enables automatic control of the length of time the heater plate 18 is energized. The processor 38 is also configured to receive data from the user controls 34 representing the desired operating temperature of the heater plate 18 and the length of time the heater plate 18 is to be energized.

The processor 38 may have access to other data stored in the memory 42, for example, flammability limits of different types of materials and lists of temperature versus the length of time needed for sterilization of different pathogens. This data can be used to display a menu via the controller front panel 30 that assists the user in setting the operating temperature and energization time of the sterilizing device 10. The user controls 34, for example, may provide a user with the option of manually setting the desired operating temperature and energization time, or an alternative option of choosing a predetermined operating temperature and energization time from the menu for a type of pathogen and a type of container (paper, plastic, cloth, or the like).

In use, the heater plate assembly 12 is placed inside a container C that will hold the objects to be sterilized that are also placed in the container. Preferably the container C is insulated to resist heat transfer from inside the container to the ambient environment. The illustrated container C shown in FIG. 5 is an insulated food carrier. Other containers that have been found satisfactory for use with the sterilizing device 10 include cardboard or stiff paper pizza boxes or the like.

Objects to be sterilized, for example, face masks, are placed in the container C and on or near the heater plate 18. The container C may then be closed to retain internal heat. The heater plate 18 is energized and the controller 14 regulates the temperature of the heater plate 18 or the air inside the container C to maintain a sufficient temperature for a sufficient length of time to sterilize the objects.

For example, the controller 14 may be set to maintain a substantially constant heater pad temperature of 200 degrees Fahrenheit or some other desired temperature below the flammability limit of the container C for a one-half hour period.

Figure 6:
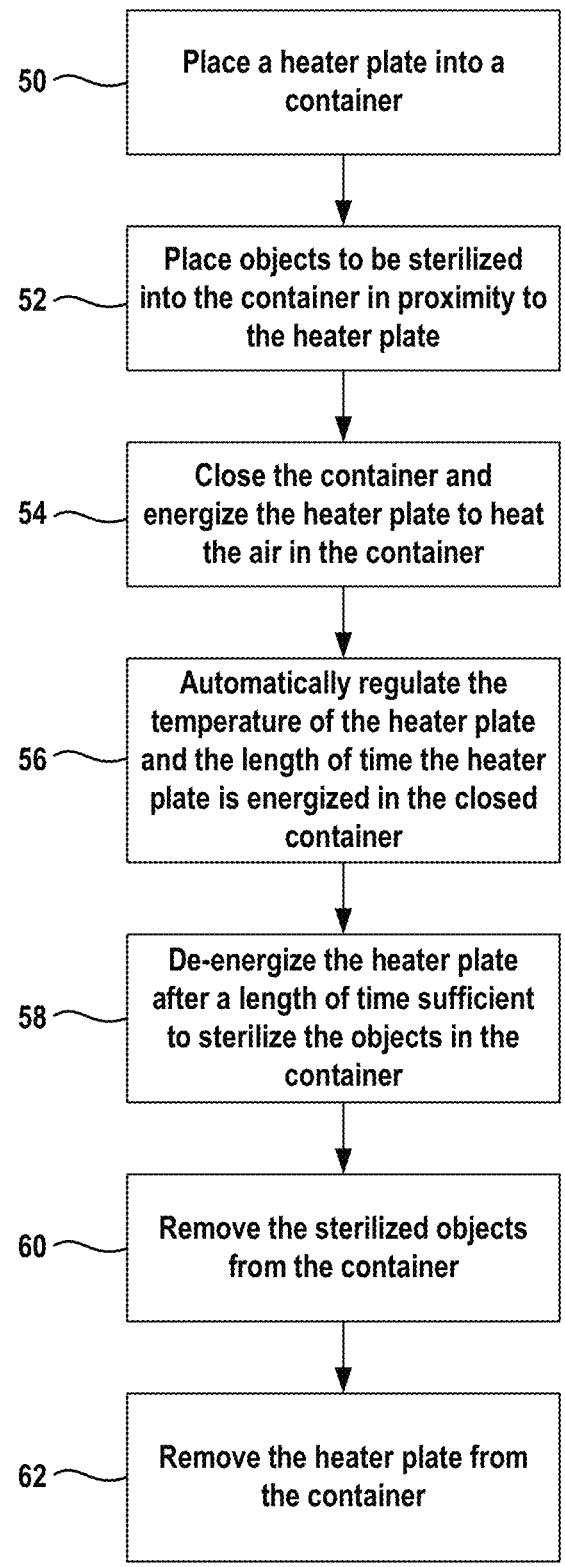
FIG. 6 illustrates the steps of a method for sterilizing objects using the sterilizing device shown in FIG. 1.

A method for sterilizing masks or other objects in accordance with this disclosure is illustrated in FIG. 6. The method may include the step 50 of placing the heater plate 18 within the container C, and the step 52 of placing objects to be sterilized in the container C with the heater plate 18 and in proximity to the heater plate 18. In the step 54 the container C is closed and the heater plate 18 energized to heat the air in the container C. In the step 56 the temperature of the heater plate 18 and length of time the heater plate is energized is automatically regulated. The heater plate 18 is then de-energized after a length of time sufficient to sterilize the objects in the container C, as shown in step 58. In the step 60, remove the sterilized objects from the container C, and in the step 52 remove the heater plate 18 from the container C.

The step 62 of removing the heater plate 18 from the container C can be performed after repeating steps 52-60 to sterilize batches of objects.

The objects being sterilized may be, as a non-limiting example, N95 masks designed to cover the nose and mouth of a wearer and help protect the wearer from breathing in some hazardous substances. N95 masks are evaluated, tested, and approved by NIOSH as per the requirements in 42 CFR Part 84 and are designed to filter out at least 95% of airborne particles. The temperature and period of time selected for energizing the heater plate is chosen to be sufficient to kill any SARS-COV-2 coronavirus present on the masks.

In other possible embodiments of the disclosed sterilizing device, the heating element may be contained inside the heater plate or may be integrally formed with the heater plate.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art including (but not limited to) changes in material selection, size, operating ranges (temperate, time, etc.), environment of use, as well as such changes and alterations that fall within the purview of the following claims.

What is claimed is:

1. A sterilizing device for sterilizing objects placed in a container, the sterilizing device comprising:
    a heater plate assembly and a controller connected to the heater plate assembly;
    the heater plate assembly comprising a heater plate and a heater that heats the heater plate, the heater plate being capable of being heated to a temperature of at least 200 degrees Fahrenheit;
    the controller comprising process control circuitry being configured to regulate the temperature of the heater plate while the heater plate is being heated by the heater;
    the heater plate assembly being spaced away from the controller wherein the heater plate assembly can be selectively placed into the container while the controller is outside of and away from the container; and
    wherein the controller process control circuitry comprises at least one sensor placeable with the heater plate assembly in a container, the sensor being configured to generate a signal representing the temperature in the vicinity of the heater plate while the heater plate is being heated.

2. The sterilizing device of claim 1 wherein the at least one sensor is a thermistor.

3. A sterilizing device for sterilizing objects placed in a container, the sterilizing device comprising:
   a heater plate assembly and a controller connected to the heater plate assembly;
   the heater plate assembly comprising a heater plate and a heater that heats the heater plate, the heater plate being capable of being heated to a temperature of at least 200 degrees Fahrenheit;
   the controller comprising process control circuitry being configured to regulate the temperature of the heater plate while the heater plate is being heated by the heater;
   the heater plate assembly being spaced away from the controller wherein the heater plate assembly can be selectively placed into the container while the controller is outside of and away from the container; and
   wherein the controller process control circuitry comprises a timer that enables the process control circuitry to control the length of time the heater plate is being energized.

4. A sterilizing device for sterilizing objects placed in a container, the sterilizing device comprising:
   a heater plate assembly and a controller connected to the heater plate assembly;
   the heater plate assembly comprising a heater plate and a heater that heats the heater plate, the heater plate being capable of being heated to a temperature of at least 200 degrees Fahrenheit;
   the controller comprising process control circuitry being configured to regulate the temperature of the heater plate while the heater plate is being heated by the heater;
   the heater plate assembly being spaced away from the controller wherein the heater plate assembly can be selectively placed into the container while the controller is outside of and away from the container; and
   wherein the controller comprises a user control connected to the controller process control circuitry, the user control operable by a user of the sterilizing to selectively set the desired temperature of the heater plate.

5. The sterilizing device of claim 4 wherein the controller process control circuitry comprises a timer that enables the process control circuitry to control the length of time the heater plate is being energized, and the user control comprises a control operable by a user to selectively set the length of time the heater plate is to be energized.

6. A method for sterilizing objects, the method comprising the steps of:
   (a) placing a heater plate into a container, the container of a type not dedicated for use in sterilizing objects;
   (b) placing the objects to be sterilized into the container in proximity of the heater plate; and
   (c) heating the heater plate to a sufficient predetermined temperature for a sufficient predetermined length of time to sterilize the objects.

7. The method for sterilizing objects of claim 6 wherein the heater plate is heated to a temperature of not less than 200 degrees.

8. The method for sterilizing objects of claim 6 wherein the heater plate is heated to temperature for at least one-half hour.

9. The method for sterilizing objects of claim 6 wherein the objects are face masks being configured to cover the nose and mouth of a wearer.

10. The method for sterilizing objects of claim 9 wherein the masks are N95 masks.

11. The method for sterilizing objects of claim 6 wherein steps (b) and (c) are repeated multiple times using the same container to sterilize batches of objects.

12. The method for sterilizing objects of claim 6 comprising the steps of:
   (d) removing the heater plate from the container after sterilizing the objects placed in the container; and
   (e) placing the heater plate into a different, second container to sterilize objects in the second container.

13. The method for sterilizing objects of claim 6 wherein in step (c) the predetermined temperature and the predetermined time are user-selectable.

* * * * *